(12) United States Patent
Balentine

(10) Patent No.: US 10,792,176 B1
(45) Date of Patent: Oct. 6, 2020

(54) KNEE BRACE

(71) Applicant: Imprint Performance, LLC, Birmingham, AL (US)

(72) Inventor: Bryan Balentine, Birmingham, AL (US)

(73) Assignee: Imprint Performance, LLC, Hoover, AL (US)

( * ) Notice: Subject to any disclaimer, the term of this patent is extended or adjusted under 35 U.S.C. 154(b) by 424 days.

(21) Appl. No.: 15/651,139

(22) Filed: Jul. 17, 2017

(51) Int. Cl.
*A61F 5/01* (2006.01)

(52) U.S. Cl.
CPC .................................. *A61F 5/0106* (2013.01)

(58) Field of Classification Search
CPC .... A61F 5/0106; A61F 5/0104; A61F 5/0102; A61F 5/01
See application file for complete search history.

(56) References Cited

U.S. PATENT DOCUMENTS

| | | | |
|---|---|---|---|
| 420,178 A | 1/1890 | Yagn | |
| 2,061,956 A | 7/1935 | Ward | |
| 4,176,665 A | 12/1979 | Tarpening | |
| 5,286,251 A | 2/1994 | Thompson et al. | |
| 5,779,655 A | 7/1998 | Holden | |
| 5,814,001 A | 9/1998 | Schwenn et al. | |
| 5,840,050 A | 11/1998 | Lerman | |
| 6,494,919 B1* | 12/2002 | Matthews | A61F 2/601 135/67 |
| 7,819,830 B2 | 10/2010 | Sindel | |
| 8,328,746 B2 | 12/2012 | Ingimundarson et al. | |
| 8,778,031 B1* | 7/2014 | Latour, Jr. | A61H 3/0288 135/65 |
| 9,101,794 B2* | 8/2015 | Ferguson, Jr. | A63B 21/00185 |
| 9,408,443 B2* | 8/2016 | Hunter | A61H 3/02 |
| 2007/0232976 A1 | 10/2007 | Castillo | |
| 2012/0296248 A1 | 11/2012 | Wayd | |
| 2012/0330203 A1 | 12/2012 | Jones | |
| 2013/0324899 A1 | 12/2013 | Lance | |
| 2014/0005584 A1 | 1/2014 | Pretz | |
| 2014/0276313 A1 | 9/2014 | Crafton et al. | |
| 2015/0032040 A1 | 1/2015 | Cadichon | |

OTHER PUBLICATIONS

Strapworks.com.

* cited by examiner

*Primary Examiner* — Tarla R Patel
(74) *Attorney, Agent, or Firm* — Bradley Arnat Boult Cummings; Timothy L. Capria

(57) ABSTRACT

A knee brace includes a body, a flexible strap, and a handle. The body is configured to support and circumferentially extend around a knee of a subject. The flexible strap includes a body end and a handle end, and the flexible strap is secured to the body at the body end; and a handle secured with the handle end of the flexible strap. The handle may include a rigid member with a gripping feature. The knee brace, or components thereof, may be constructed of an elastic synthetic polymer, such as nylon.

9 Claims, 3 Drawing Sheets

KNEE BRACE

TECHNICAL FIELD

The present disclosure relates to a knee brace. More specifically, the disclosure is directed towards a knee brace that includes a body configured to circumferentially extend around a knee of a subject, a flexible strap including a body end and a handle end and secured to the body at the body end, and a handle secured with the handle end of the flexible strap.

BACKGROUND OF INVENTION

Knee braces, or knee orthoses, are commonly employed to resist excessive movement of the knee joint in humans. In particular, knee braces provide support to the patella and surrounding ligaments. Knee braces are used during physical activity, such as sports, recovering from an injury, and to prevent injury. In instances where a knee brace is used with subjects having diseases causing impairment of muscles surrounding the knee, the knee brace can prevent flexion or extension instability of the knee.

Because knee braces are generally desired to provide stability to the knee without excessively limiting range of motion in the subject, existing knee braces are not positionally secure, or do not allow the subject to adjust the position of the knee brace without excessively limiting range of motion in the subject. Thus, a need exists for knee braces that can be positionally adjusted or secured with the subject while the subject maintains a sufficient range of motion.

BRIEF SUMMARY

In one aspect, a knee brace includes a body configured to circumferentially extend around a knee of a subject. The knee brace has a flexible strap including a body end and a handle end. The flexible strap is secured to the body at the body end. The knee brace includes a handle secured with the handle end of the flexible strap. The body may include a plurality of supports configured to circumferentially extend around the knee. The plurality of supports may include a superior support, an inferior support, and a center support disposed between the superior support and the inferior support. Each of the plurality of supports may be connected to a leg member that extends substantially parallel to a sagittal plane of the subject. The body end may be secured with the superior support. Some embodiments of the knee brace have a body that includes a medial portion and a lateral portion disposed opposite from the medial portion, with the flexible strap secured to the lateral portion of the body.

In an embodiment of the knee brace, the flexible strap is constructed of an elastic synthetic polymer. The elastic synthetic polymer can be, for example, nylon. The handle may include a rigid member. The flexible strap may be releasably secured with the body.

In a second aspect, a knee brace includes a body configured to circumferentially extend around a knee of a subject. The body includes a plurality of supports configured to a circumferentially extend around the knee. The plurality of supports include a superior support, an inferior support, and a center support disposed between the superior support and the inferior support. Each of the plurality of supports is connected to a leg member that extends substantially parallel to a sagittal plane of the subject. A flexible strap is configured to vertically secure the superior support with a belt or a belt loop. In some embodiments of the knee brace, the body includes a medial portion and a lateral portion disposed opposite from the medial portion, and the flexible strap is secured to the lateral potion. The knee brace may include a fastener, such as a self-locking clasp, configured to secure the flexible strap with the belt or the belt loop. The knee brace may include an additional flexible strap configured to vertically secure the inferior support with a foot member or vertically secure the superior support with a torso member or a shoulder member.

In another aspect, a knee brace includes a body configured to circumferentially extend around a knee of a subject. The body has a plurality of supports configured to circumferentially extend around the knee. The plurality of supports include a superior support, an inferior support, and a center support disposed between the superior support and the inferior support. Each of the plurality of supports connects to a leg member extending substantially parallel to a sagittal plane of the subject. A flexible strap is configured to vertically secure the inferior support with a foot member. The foot member is dimensioned to receive at least a portion of a foot of the subject. In an embodiment of the knee brace, an additional flexible strap is configured to vertically secure the superior support with a belt or a belt loop or to vertically secure the superior support with a torso member or a shoulder member.

BRIEF DESCRIPTION OF DRAWINGS

It should be noted that identical features in different drawings are shown with the same reference numeral.

DETAILED DESCRIPTION

Figure 1:
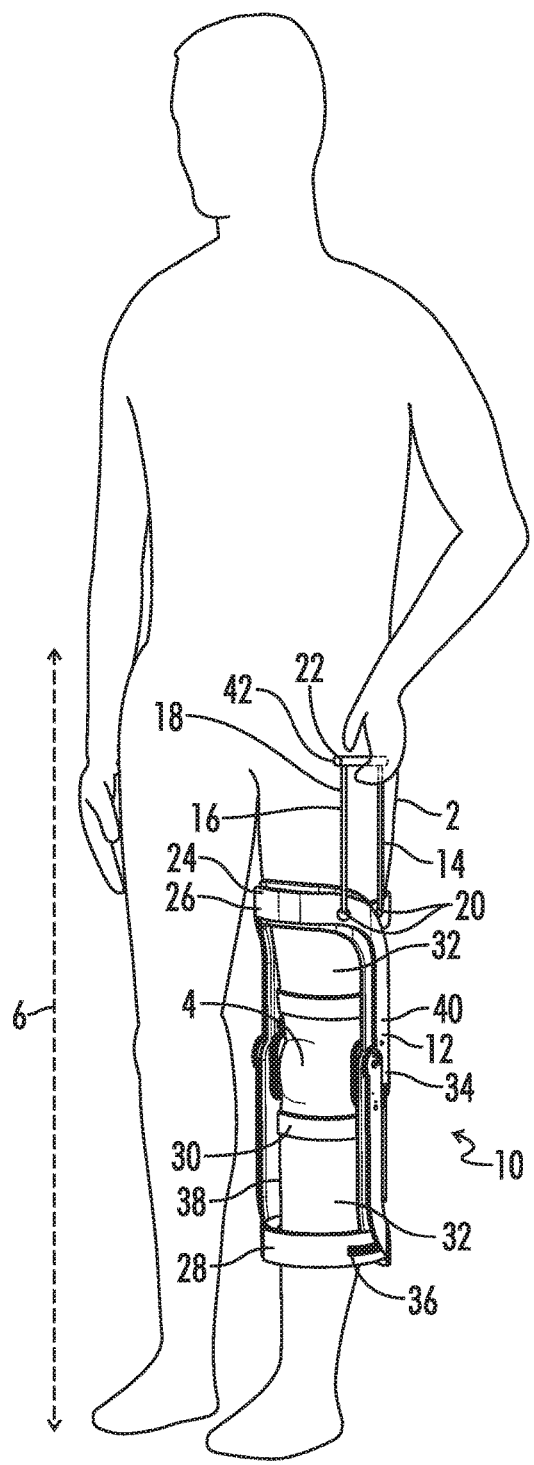
FIG. 1 shows a front perspective view of one embodiment of a knee brace.

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations as come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limited the broader aspects of the present disclosure.

For the sake of clarity, not all reference numerals are necessarily present in each drawing Figure. In additional, positional terms such as "upper," "lower," "side," "top," "bottom," "vertical," "horizontal," etc. refer to the knee brace when in the orientation shown in the drawings. The skilled artisan will recognize that the knee brace can assume different orientations when in use.

A knee brace has been developed. The knee brace of the present disclosure is intended to retain a position on a subject while still allowing the subject to have a comfortable range of motion while wearing the knee brace. The knee brace resists migration and/or can be easily adjusted by the subject to a desired position to continue to provide support in the desired area on the subject.

One embodiment of the knee brace is shown in FIG. 1. In this embodiment, a knee brace 10 includes a body 12 configured to circumferentially extend around a knee region 4 and/or tissue surrounding the knee region 4 of a subject 2. The body 12 may be constructed of, for example, any suitable material such as one or more metals, a polymer such as neoprene, an alloy, or any combination thereof. A strap 14 is provided on the body 12.

The strap 14 includes a body end 16 disposed toward the body 12 and a handle end 18 disposed oppositely to the body end 16 when the strap is in an extended position, as shown. The strap 14 may be flexible or rigid. The strap 14 may be constructed of any suitable material, such as a rigid polymer or an elastic flexible polymer such as nylon. The strap 14 may be releasably coupled, or attached, with the body 12 at least one strap connection member 20. By way of example, the handle connection member 20 may be a hook and loop fastener, a snap, a zipper, a buckle, a clasp, a button, a grommet, or any combination thereof. A handle 22 is disposed at the handle end of the strap 14 and secured to the body 12 by the strap 14. The handle 22 may be rigid or flexible, and the handle 22 may have a rigid member 42 disposed thereon. The handle 22 or rigid member 42 may include at least one gripping member 24 disposed thereon such that a user can conveniently and ergonomically grip the handle 22.

The knee brace 10 may include a plurality of supports 24, each plurality of support 24 configured to circumferentially extend around the knee region 4 and secured by a leg member 34 on the body 12. The leg member 34 may extend substantially parallel to a sagittal plane 6 of the subject 2. Alternatively, the knee brace 10 may have a single support 24 (not shown) configured to circumferentially extend around the knee region 4. The plurality of supports 24 may include a superior support 26 positioned at the upper end of the knee brace 10. The plurality of supports 24 may include an inferior support 28 positioned at the lower end of the knee brace 10. The plurality of supports 24 may include a center support 30 disposed within the superior support 26 and the inferior support 28. The plurality of supports 24 may define a plurality of apertures 32, each aperture disposed between two supports 24. Advantageously, in embodiments of the knee brace 10 having the plurality of supports 24 and plurality of apertures 32, the knee brace 10 is lightweight, provides support to the knee region 4, and is breathable for the subject 2. The plurality of supports 24 may be have an adjustable feature 36, such as a hook and loop fastener, to fit on the knee regions 10 of different sizes and ages of subjects 2.

The strap 14 may be positioned on and secured with the plurality of supports 24, such as the superior support 26, the inferior support 28, the center support 30 (as shown), or any combination thereof. Advantageously, the handle 22 and strap 14 may be configured and dimensioned such that when the handle 22 and the strap 14 are in the extended position, handle 22 is conveniently reachable for the subject 2, and when the handle 22 and the strap 14 are in a relaxed position, the handle 22 and the strap 14 do not reach the ground. This feature prevents the handle 22 from being a tripping hazard for the subject 2 while maintaining convenient access for the subject 2. The strap 14 may be constructed of any suitable material, such as a rigid polymer or an elastic flexible polymer such as nylon.

Problematically, conventional knee braces migrate, or slide, down the leg of the subject when they are in-use. When the conventional knee braces migrate, they are unable to provide adequate support to the associated knee region and become uncomfortable. However, in embodiments of the knee brace 10 having the strap 14 and the handle 22, the subject 2 can readjust (i.e., pull upwardly) on the brace 10 to restore the brace 10 to its desired position to maintain efficacy and comfort.

As shown in FIG. 1, the body 12 includes a medial portion 38 (i.e., the inner portion) and a lateral portion 40 (i.e., an oppositely outwardly facing portion) disposed opposite from the medial portion. The strap 14 may be secured to the lateral portion 40 of the body 12. Advantageously, in embodiments of the knee brace 10 having strap 14 secured to the lateral portion 40 of the body 12, the positioning of the strap 14 allows the subject 2 to conveniently reach the handle 22, as the handle 22 is in, or proximate to, a plane 6 running lengthwise to the subject's arm.

Figure 2:
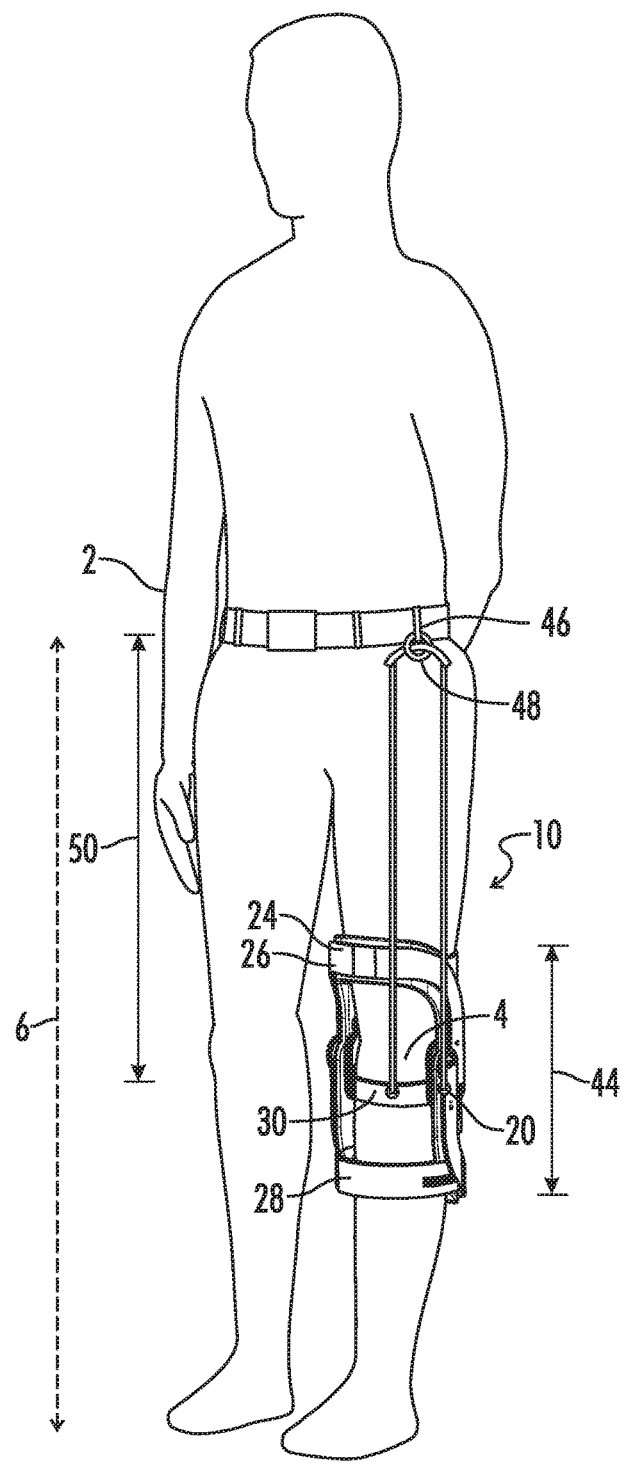
FIG. 2 shows a front perspective view of another embodiment of a knee brace.

As shown in FIG. 2, an embodiment of the knee brace 10 has the body 12 configured to circumferentially extend around the knee region 4 of the subject 2. The body 12 includes a length 44 extending parallel to the plane 6. The plurality of supports 24 are configured and dimensioned to extend circumferentially around the knee region 4. The plurality of supports 24 include the superior support 26, the inferior support 28, and the center support 30 disposed within, or between, the superior support 26 and the inferior support 28. Each of the plurality of supports 24 is coupled with, or attached to, the leg member 34 at the at least one strap connection member 20. The leg member 34 extends substantially parallel to the sagittal plane 6. The flexible strap 14 is configured to vertically secure one or more of the plurality of supports 24, such as the superior support 26 or the center support 30 (as shown in FIG. 2) with a belt or a belt loop 46. The flexible strap 14 may releasably attach to the belt or belt loop 46 with a fastener 48, such as, by way of example, a loop, a hook, a button, a hook, or a self-locking clasp.

The strap 14 may be dimensioned to extend a length 50 of about 25% to 250% of a body length 44 of the body 12. When the strap 14 is secured with belt or belt loop 46, the belt or belt loop 46 provides vertical support such as to prevent the knee brace 10 from migrating downwards. The strap 14 may be constructed of any suitable material, such as a rigid polymer or an elastic flexible polymer such as nylon.

Figure 3:
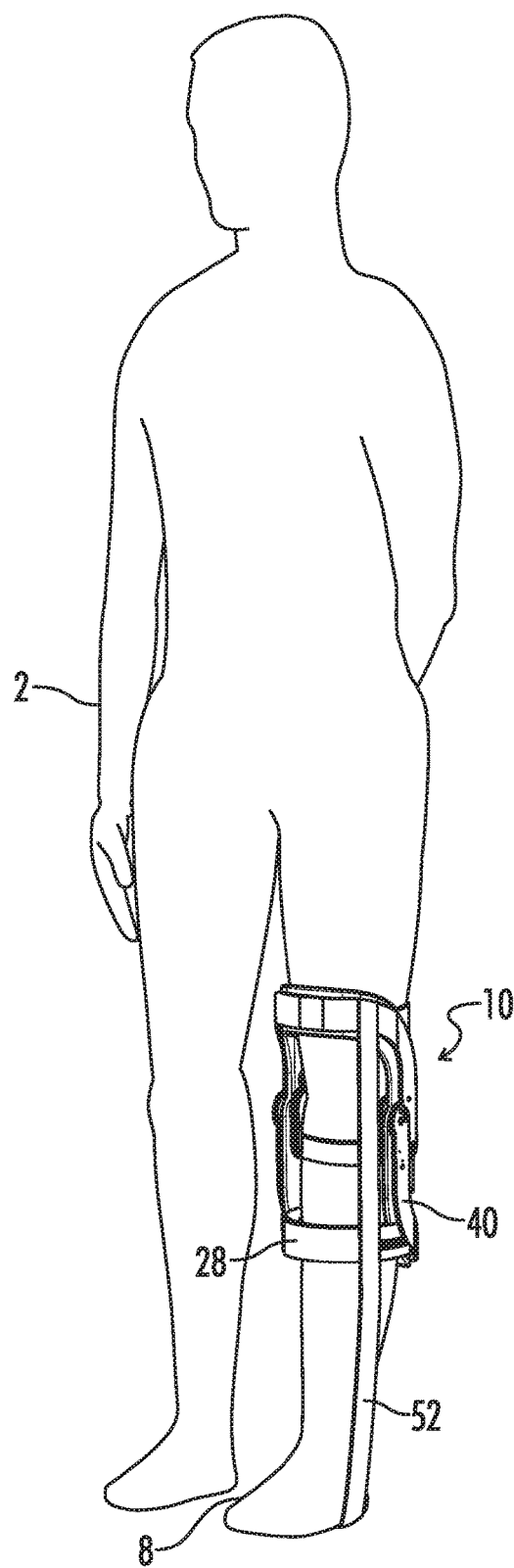
FIG. 3 shows a front perspective view of a yet another embodiment of a knee brace.

As illustrated in FIG. 3, an embodiment of the knee brace 10 includes the flexible strap 14 configured to vertically secure one or more of the plurality of supports 24, such as the inferior support 28, with a foot member 52. The foot member 52 may be configured and dimensioned to receive at least a portion of a foot 8 of the subject 2. For example, the foot member 52 may extend from the leg member 34 on both the lateral portion 40 and the medial portion 38 of the brace 10 such that the foot member 52 is dimensioned and configured to receive the heel area of the foot 8. The foot member 52 may extend from one or more of the plurality of supports 24. When the foot member 52 is in use, the foot member vertically secures the knee brace 10 to prevent migration, including vertical, lateral, and rotational migration.

Figure 4:
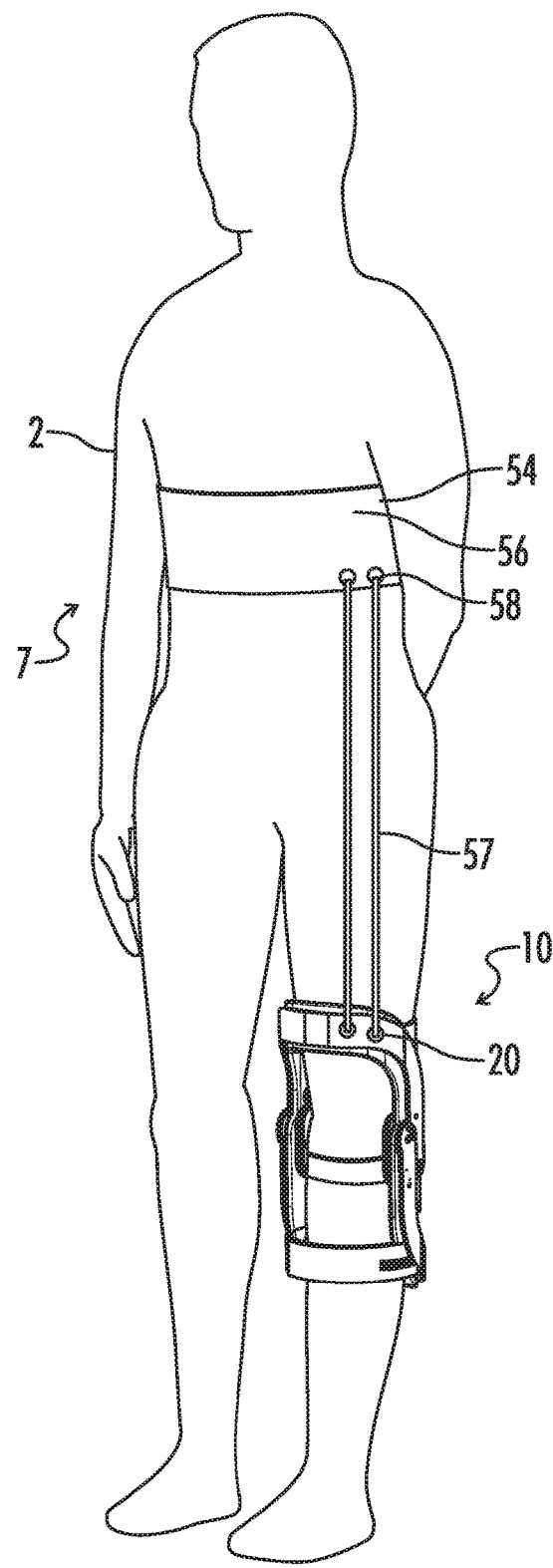
FIG. 4 shows a front perspective view of a yet another embodiment of a knee brace.
Figure 5:
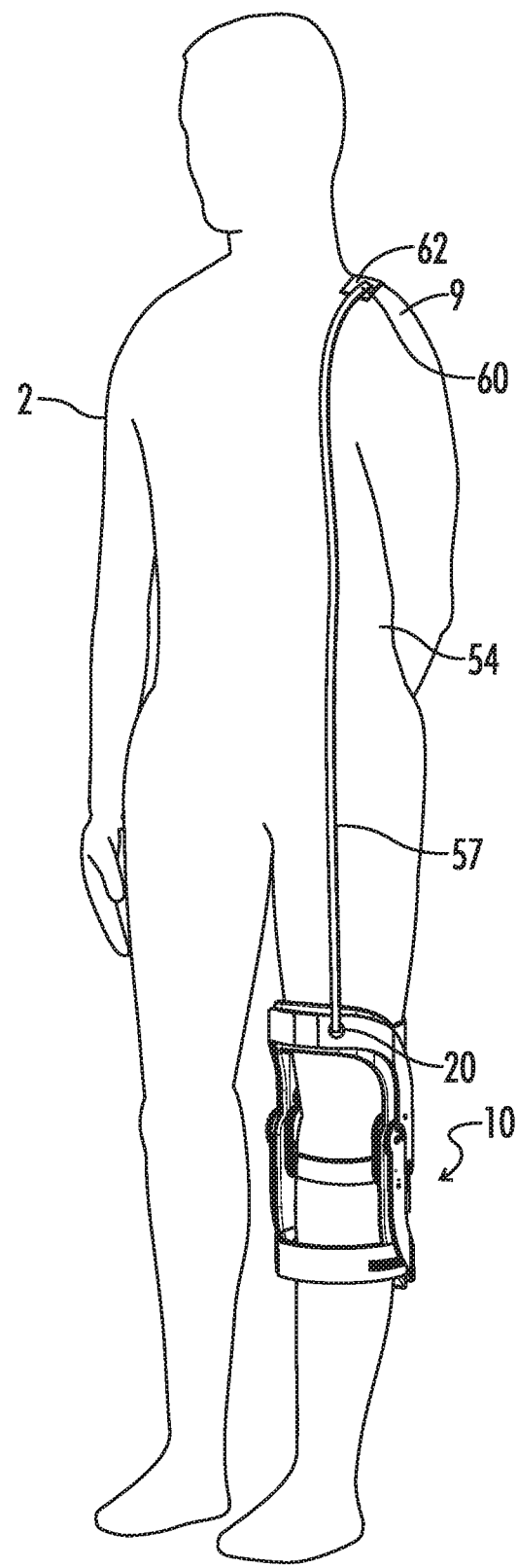
FIG. 5 shows a front perspective view of a further embodiment of a knee brace.

As shown in FIGS. 4 and 5, an embodiment of the knee brace 10 includes an upper member 54 configured to vertically secure the knee brace 10. The upper member 54 may attach to various points on the subject 2 above the waist. As illustrated in FIG. 4, the upper member 54 may comprise a torso member 56 that extends circumferentially on a torso 7 of the subject 2. The upper member 54 may include an additional flexible strap 57 that releasably couples with each of the knee brace 10 at the at least one strap connection member 20 and the upper member 54 at an upper member connection member 58, independently. Advantageously, in embodiments of the knee brace 10 having torso member 56, the knee brace is vertically secured, and forces from exerted from the knee brace 10 are distributed across torso member 56 for subject comfort. The upper member may attach to the knee brace 10 at the at least one strap connection member 20.

As illustrated in FIG. 5, the upper member 54 may comprise a shoulder member 60. Shoulder member 60 is configured and dimensioned to extend over a shoulder 9 of the subject 2. The shoulder member 60 may comprise a shoulder pad 62 so as to distribute weight and pressure across the shoulder 9 when the knee brace 10 is in use. The shoulder member 60 may extend from the knee brace 10 both on the dorsal and ventral side of the patient 2, providing vertical support to the knee brace 10 to maintain the knee brace 10 in a desired position. The shoulder member 60 may be configured to be worn on the shoulder 9 on the same side of the body on which the knee brace 10 is worn, or the shoulder member 60 may be configured to be worn on the shoulder 9 on the other side of the body.

Although embodiments of the disclosure have been described using specific terms, devices, and methods, such description is for illustrative purposes only. The words are words of description rather than of limitation. It is to be understood that changes and variations may be made by those of ordinary skill in the art without departing from the sprit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described particular embodiments of the present invention of a new and useful knee brace, it is not intended that such references be construed as limitations upon the scope of this invention except as set forth in the following claims.

What is claimed is:

1. A knee brace, comprising:
   a body configured to circumferentially extend around a knee of a subject to provide support to a patella and one or more ligaments surrounding the patella when the knee brace is worn by the subject in a standing, straight leg position, the body including
      a leg member extending substantially parallel to a sagittal plane of the subject, and
      a plurality of supports configured to circumferentially extend around the knee, the plurality of supports including a superior support, an inferior support, and a center support disposed between the superior support and the interior support, each of the plurality of supports connected to the leg member;
   a strap including a body end and a handle end, the strap secured to the body at the body end; and
   a handle secured with the handle end of the strap and configured to pull the body upwardly on the knee when the knee brace is worn by the subject.

2. The knee brace of claim 1, wherein the body end is secured with the superior support.

3. The knee brace of claim 1, wherein the body includes a medial portion and a lateral portion disposed opposite from the medial portion, and wherein the strap is secured to the lateral portion of the body.

4. The knee brace of claim 1, wherein the strap is constructed of an elastic synthetic polymer.

5. The knee brace of claim 4, wherein the elastic synthetic polymer includes nylon.

6. The knee brace of claim 1, wherein the handle includes a rigid member.

7. The knee brace of claim 1, wherein the strap is releasably secured with the body.

8. The knee brace of claim 1, wherein the strap is flexible.

9. The knee brace of claim 1, wherein the strap is rigid.

* * * * *